US012458483B2

(12) United States Patent
Minion

(10) Patent No.: US 12,458,483 B2
(45) Date of Patent: Nov. 4, 2025

(54) ENDOLUMINAL GRAFT SYSTEM AND METHOD OF IMPLANTING THE SAME

(71) Applicant: University of Kentucky Research Foundation, Lexington, KY (US)

(72) Inventor: David Jon Minion, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1439 days.

(21) Appl. No.: 16/861,036

(22) Filed: Apr. 28, 2020

(65) Prior Publication Data

US 2020/0253712 A1 Aug. 13, 2020

Related U.S. Application Data

(60) Division of application No. 15/849,329, filed on Dec. 20, 2017, now Pat. No. 10,667,899, which is a (Continued)

(51) Int. Cl.
*A61F 2/07* (2013.01)
*A61F 2/95* (2013.01)
(Continued)

(52) U.S. Cl.
CPC .................. *A61F 2/07* (2013.01); *A61F 2/95* (2013.01); *A61F 2/954* (2013.01);
(Continued)

(58) Field of Classification Search
CPC .... A61F 2/07; A61F 2/95; A61F 2/954; A61F 2002/061; A61F 2002/067;
(Continued)

(56) References Cited

U.S. PATENT DOCUMENTS

2013/0289702 A1 10/2013 Coghlan et al.
2014/0324150 A1 10/2014 Stephens et al.

OTHER PUBLICATIONS

"How To Maximize The Benefits Of The Sealing Zone In The Ovation Endograft: Tips And Tricks" VEITH Symposium New York, NY. Nov. 18-22, 2014.

(Continued)

*Primary Examiner* — Leslie A Lopez
(74) *Attorney, Agent, or Firm* — Stites & Harbison PLLC; James R. Hayne

(57) ABSTRACT

An endoluminal graft system comprising an endoluminal graft including a framework and a flexible fabric surrounding the framework, a deflection means configured for placement through an opening to a branching vessel, and a delivery catheter configured to position the endoluminal graft within a primary vessel. A method of implanting the endoluminal graft includes positioning the endoluminal graft within a primary vessel with a leading edge of the endoluminal graft adjacent to an opening to a branching vessel. A deflecting means is positioned through the opening to the branching vessel adjacent to the leading edge of the endoluminal graft. The endoluminal graft is then advanced along the length of the primary vessel with the deflection means engaging the leading edge of the endoluminal graft to form a scallop along the leading edge of the endoluminal graft.

6 Claims, 14 Drawing Sheets

Related U.S. Application Data continuation of application No. 15/352,516, filed on Nov. 15, 2016, now abandoned.

(60) Provisional application No. 62/255,496, filed on Nov. 15, 2015.

(51) Int. Cl.
*A61F 2/954* (2013.01)
*A61F 2/06* (2013.01)

(52) U.S. Cl.
CPC ... *A61F 2002/061* (2013.01); *A61F 2002/067* (2013.01); *A61F 2240/001* (2013.01)

(58) Field of Classification Search
CPC ...... A61F 2240/001; A61F 2/915; A61F 2/06; A61F 2/94; A61F 2/945
See application file for complete search history.

(56) References Cited

OTHER PUBLICATIONS

"The value of polymer-filled sealing ring technology for abdominal aortic aneurysm" Charing Cross Symposium London, England. Apr. 28-May 1, 2015.
"Ovation Endograft From TriVascular For EVAR: Advantages And Tips And Tricks For Use." VEITH Symposium New York, NY. Nov. 17-21, 2015.
"Patency matters" LINC Leipzig, Germany. Jan. 26-29, 2016.

ENDOLUMINAL GRAFT SYSTEM AND METHOD OF IMPLANTING THE SAME

CROSS-REFERENCE TO RELATED APPLICATIONS

The present application is divisional of U.S. patent application Ser. No. 15/849,329 filed on Dec. 20, 2017, which is a continuation of U.S. patent application Ser. No. 15/352,516 filed on Nov. 15, 2016, which claims priority to U.S. Provisional Patent Application Ser. No. 62/255,496 filed on Nov. 15, 2015, the entire disclosures of which are incorporated herein by reference.

TECHNICAL FIELD

The present invention relates to an endoluminal graft system and method of implanting the same. In particular, the present invention relates to a system and method in which scallops are formed in-situ during the delivery and deployment of an endoluminal graft.

BACKGROUND OF THE INVENTION

An aneurysm is a degenerative dilation of a portion of a blood vessel that can ultimately lead to rupture of the vessel and life-threatening blood loss. As shown in FIG. 1, one of the most common sites of an aneurysm 105 is the infra-renal aorta 101 between the renal arteries 102 and the iliac vessels 106.

Referring now to FIG. 2, endovascular aneurysm repair (EVAR) is a minimally invasive procedure, which involves placing a tubular prosthesis 110 within the diseased blood vessel to act as an impervious liner which prevents the systemic pressure from pushing on the aneurysm 105. In particular, such prostheses 110 are generally made of a blood-impervious fabric such as polytetrafluorethylene (PTFE) or polyester (PET) that is supported along at least a portion of its length by a framework or skeleton. The framework or skeleton is commonly a metal (e.g., nitinol, stainless steel, chromium cobalt, etc.) or an injectable polymer. To be effective, the prosthesis must achieve circumferential wall apposition (or seal) with the inner wall of a healthy portion of the blood vessel, or vessels, proximal and distal to the aneurysm 105. For standard EVAR, the proximal seal is made in a healthy portion 104 of the aorta 101 distal to the openings 103 of the renal arteries 102. As shown in FIG. 2, since most infra-renal aneurysms extend to the terminal bifurcation of the aorta 101, most endovascular prostheses 110 for this location incorporate a bifurcated design, allowing for the distal seal to be achieved in each of the iliac vessels 106.

Referring still to FIG. 2, many endovascular prostheses 110 consist of a flat-topped fabric supported by a framework configured as a series of peaks and indentations. To achieve an effective seal, the proximal end of the graft 110 must have circumferential wall contact with the healthy portion 104 of the aorta 101. It is generally recommended that the longitudinal length of the healthy portion 104 of the aorta 101 be at least 15 mm to achieve a seal of sufficient length to ensure a long-term successful seal. However, in some cases, the aneurysm 105 arises too close to the renal arteries 102 to achieve this length of seal.

One known solution is to use an endoluminal graft with a scallop formed in the fabric of the endoluminal graft. A scallop, as used herein, is a deflection or discontinuity of the normally straight edge of the fabric of the endoluminal graft.

Such scallops, can allow preservation of flow to important branch vessels such as the renal arteries that arise in the intended seal zone of the endoluminal graft. However, scallops require custom manufacture of a graft based on the patient's anatomy, an issue which is complicated when more than one scallop is required. Furthermore, extreme care must be taken to ensure that the scallops are properly aligned with the branch vessel during deployment of the endoluminal graft in order to avoid obstructing blood flow into the branch vessel.

SUMMARY OF THE INVENTION

The present invention is an endoluminal graft system and method of implanting the same in which scallops are formed in-situ during the delivery and deployment of the endoluminal graft, thereby ensuring proper alignment of the scallop with the branching vasculature and obviating the need for custom manufacturing of grafts with preformed scallops.

An exemplary endoluminal graft, or graft, used as part of the system and method of the present invention generally comprises a framework and a flexible fabric surrounding the framework. The framework of the graft includes a plurality of curvilinear elements with an uppermost element defining a plurality of alternating peaks and indentations. Furthermore, the flexible fabric defines a leading edge which initially extends between the peaks substantially flat across the indentations defined by the framework of the graft. In this way, the leading edge of the flexible fabric is also the leading edge of the graft. Furthermore, because a portion of the flexible fabric extends above the framework (i.e., across the indentations), the leading edge of the flexible fabric is deformable, as further discussed below.

In a first step of an exemplary implementation of the method of the present invention, the graft is positioned within a primary vessel, such as the aorta, extending through an aneurysm and into a healthy portion of the aorta with the leading edge of the flexible fabric adjacent to an opening to a branching vessel, or vessels, such as the renal arteries. As previously mentioned, when the graft is first positioned within the aorta, the leading edge of the flexible fabric extends substantially flat between the peaks of the framework.

After positioning the graft with the leading edge adjacent to the openings of the renal arteries, a deflection means, for example a balloon, is positioned through the opening of each of the renal arteries and subsequently inflated. In other words, a distal portion of the balloon is positioned and temporarily secured within the renal artery while a proximal portion of the balloon remains within the aorta itself. The balloon therefore acts as a physical extension of the renal arteries into the aorta.

After the balloons are positioned and inflated, the graft is advanced along the length of the aorta, such that the balloons engage the leading edge of the flexible fabric and cause the flexible fabric to deflect and form scallops along the leading edge of the flexible fabric and within the indentations of the framework. Advantageously, since the balloons are inflated so as to be secured within the renal arteries, the scallops are aligned with each of the renal arteries. That is to say, the system and method of the present invention are configured such that the balloons, or other such deflection means, align the indentations of the framework with the renal arteries so that the resulting scallops are also properly aligned with the renal arteries. In particular, as the graft is advanced along the length of the aorta and the balloons begin to deflect the flexible fabric, the balloons engage the indentations of the underlying framework. As the balloons slide down the framework and into the indentations, the balloons cause the graft to rotate so as to aligned the indentation with the balloon extending from the renal artery. The resulting scallops formed within the indentation are therefore aligned with the balloons and no scallops are formed along the portion of the leading edge where the balloons are not present, as further discussed below.

The balloons are, in some exemplary implementations of the method of the present invention, introduced by a distal approach, such that the balloons pass through the graft itself before being positioned through the openings of the renal arteries, but in other exemplary implementations of the present invention, the balloons are introduced by a proximal approach.

After the scallops are formed along the leading edge of the graft, the balloons are deflated and removed from the openings to the renal arteries. The graft is now positioned within the aorta with a proximal seal made in the healthy portion of the aorta proximal to the aneurysm. Advantageously, in the exemplary system and method of the present invention, it is only the portions of the leading edge of graft which are aligned with the openings to the renal arteries (i.e., where the balloons were previously positioned) that is deflected to create the scallops. The remaining portion of the leading edge is not deflected and extends above the openings to the renal arteries. As such, even when the aneurysm is relatively close to the renal arteries, the area of the flexible fabric in contact with the healthy portion of the aorta provides a sufficient seal while still preserving blood flow to the renal arteries.

Further features and advantages of the present invention will become evident to those of ordinary skill in the art after a study of the description, figures, and non-limiting examples in this document.

DESCRIPTION OF THE INVENTION

The present invention relates to the design of endoluminal graft systems, which are medical devices designed to treat vascular pathology such as aneurysms or dissections and methods of implanting the same. More specifically, the invention is an endoluminal graft system, and method of implanting the same, in which scallops are formed in-situ during the delivery and deployment of the endoluminal graft, thereby ensuring proper alignment of the scallop with the branching vasculature and obviating the need for custom manufacturing of grafts with preformed scallops.

Figure 1:
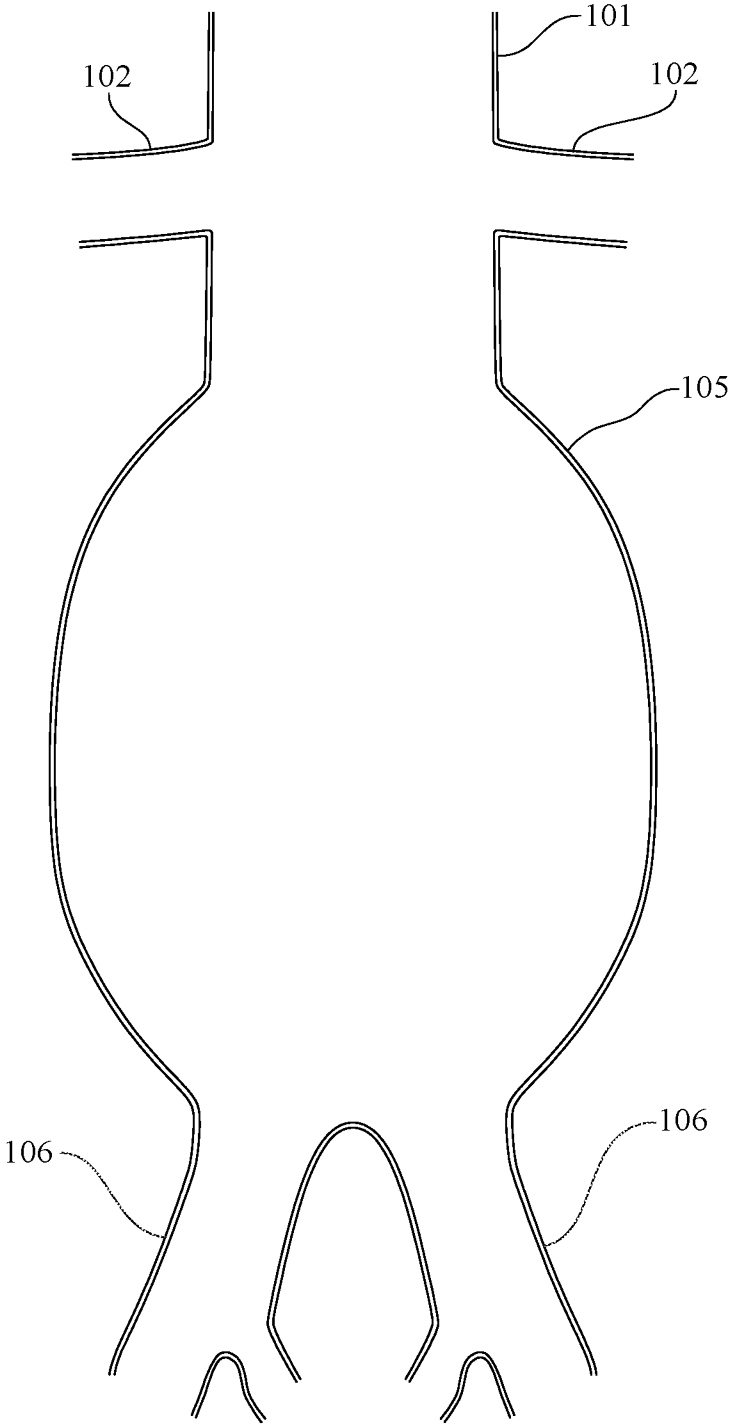
FIG. 1 depicts an aneurysm in the infra-renal aorta of a patient's vasculature.
Figure 2:
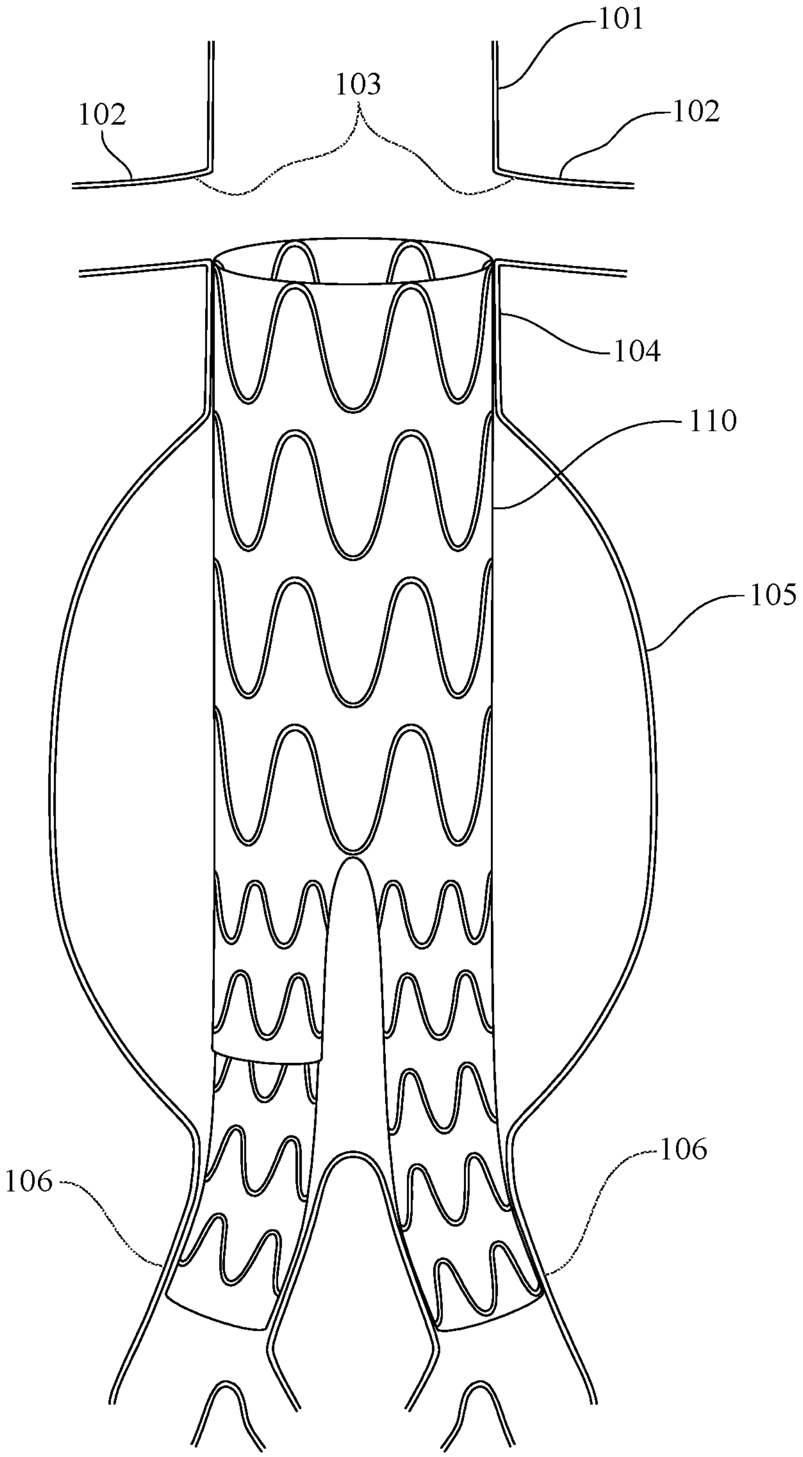
FIG. 2 (PRIOR ART)
FIG. 2 depicts an endoluminal graft known in the prior art deployed within the vasculature of FIG. 1.
Figure 3:
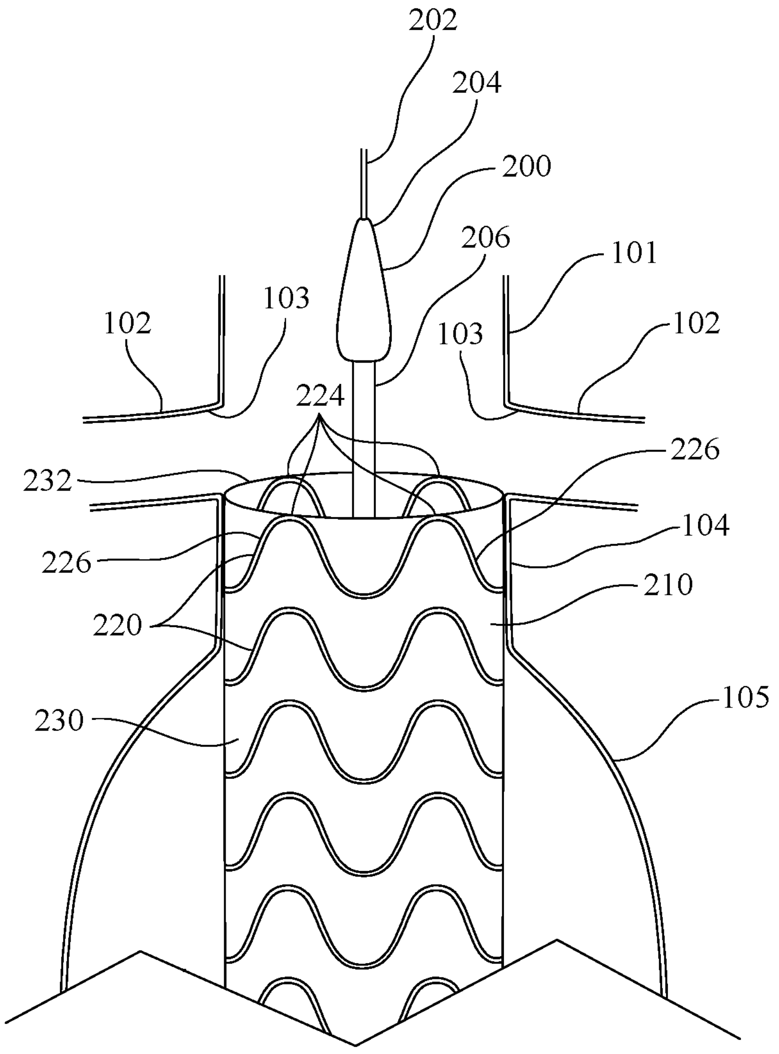
FIG. 3 depicts a proximal seal zone of an exemplary endoluminal graft of the present invention positioned via a delivery catheter.

Referring now to FIGS. 3-6, an exemplary endoluminal graft, or graft, 210 used as part of the system and method of the present invention generally comprises a framework 220 and a flexible fabric 230 surrounding the framework 220. The framework 220 of the graft 210 includes a plurality of curvilinear elements with an uppermost element defining a plurality of alternating peaks 224 and indentations 226. Furthermore, the flexible fabric 230 defines a leading edge 232 which, as shown in FIG. 3, initially extends between the peaks 224 substantially flat across the indentations 226 defined by the framework 220 of the graft 210. In this way, the leading edge 232 of the flexible fabric 230 is also the leading edge 232 of the graft 210. Furthermore, because a portion of the flexible fabric 230 extends above the framework 220 (i.e., across the indentations 226), the leading edge 232 of the flexible fabric 230 is deformable, as further discussed below.

Referring now specifically to FIG. 3, in a first step of an exemplary implementation of the method of the present invention, the graft 210 is positioned within a primary vessel of a patient, such as the patient's aorta 101, extending through an aneurysm 105 and into a healthy portion 104 of the aorta 101 with the leading edge 232 of the flexible fabric 230 adjacent to an opening 103 to a branching vessel, or vessels, such as the renal arteries 102. As previously mentioned, when the graft 210 is first positioned within the aorta 101, the leading edge 232 of the flexible fabric 230 extends substantially flat between the peaks 224 of the framework 220.

Although not shown in the Figures, it should be understood by one skilled in the art that the graft 210 may be positioned by way of the patient's femoral artery or by other common techniques. Typically, the graft 210 is placed in communication with the interior of the patient's vessel while the graft 210 is in an undeployed configuration which is substantially narrower than the fully deployed configuration. In some embodiments, a delivery sheath or other similar device known in the art, may further assist in placement of the graft 210, however, in other embodiments a delivery sheath may not be needed. In either event, as shown in FIG. 3, the delivery sheath and/or graft 210 are guided by a delivery catheter 200 into position within the aorta 101, and, subsequently, the graft 210 is deployed. As shown in the Figures, the delivery catheter 200 includes a nose cone 204 which is advanced along a guidewire 202 and which precedes a guidewire lumen 206 that is disposed around the guidewire 202.

Figure 4A:
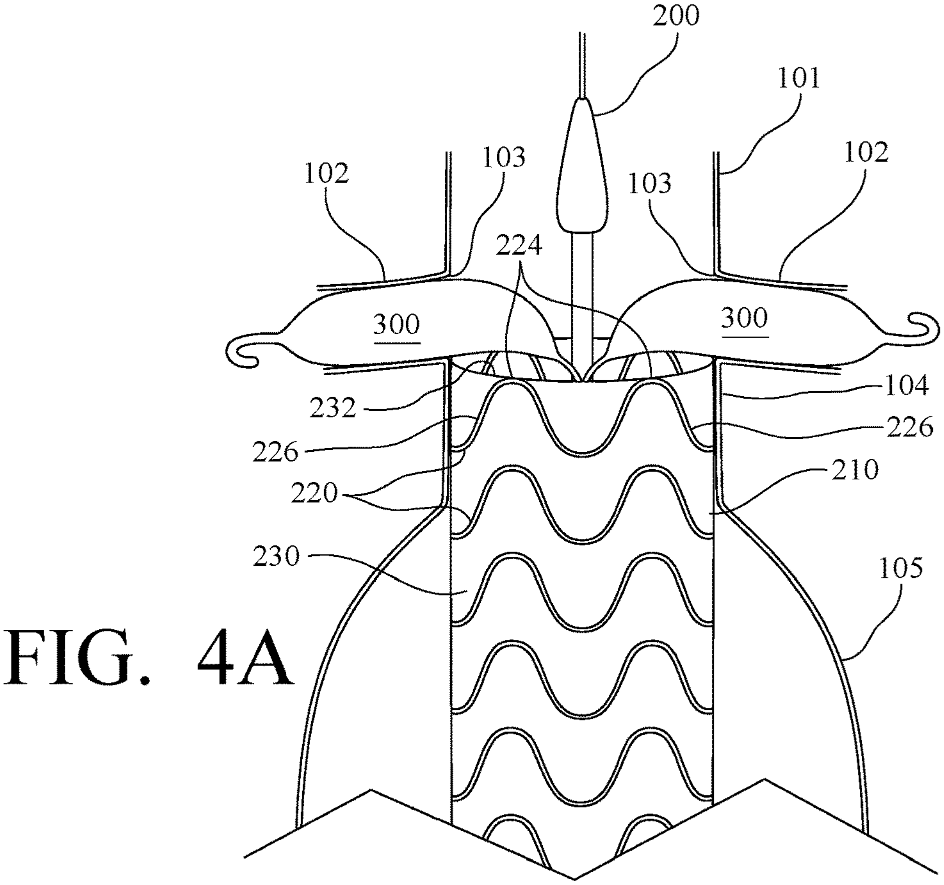
FIG. 4A depicts the proximal seal zone of FIG. 3 with two balloons, introduced by a distal approach, positioned and inflated within each of the renal arteries.

Referring now specifically to FIG. 4A, after positioning the graft 210 with the leading edge 232 adjacent to the openings 103 of the renal arteries 102, a deflection means 300, which in the embodiment shown in FIG. 4A is a balloon 300, is positioned through the opening 103 of each of the renal arteries 102 and subsequently inflated. In other words, and as shown in FIG. 4A, a distal portion of the balloon 300 is positioned and temporarily secured within the renal artery 102 while a proximal portion of the balloon 300 remains within the aorta 101 itself. The balloon 300 therefore acts as a physical extension of the renal arteries 102 into the aorta 101.

Figure 5A:
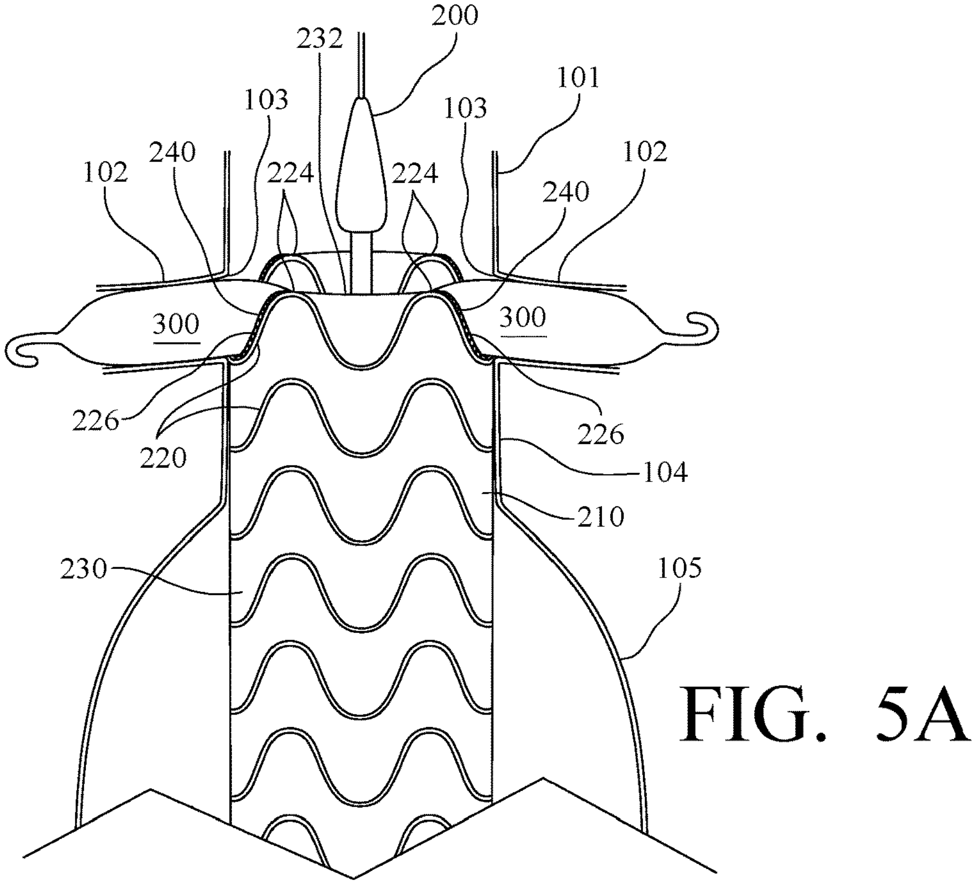
FIG. 5A depicts the proximal seal zone of FIG. 4A after the graft is advanced and each balloon has formed a scallop in the leading edge of the flexible fabric.

Referring now specifically to FIG. 5A, after the balloons 300 are positioned and inflated, the graft 210 is advanced along the length of the aorta 101, such that the balloons 300 engage the leading edge 232 of the flexible fabric 230 and cause the flexible fabric 230 to deflect and form scallops 240 along the leading edge 232 of the flexible fabric 230 and within the indentations 226 of the framework 220. Advantageously, since the balloons 300 are inflated so as to be secured within the renal arteries 102, the scallops 240 are aligned with each of the renal arteries 102. That is to say, the system and method of the present invention are configured such that the balloons 300, or other such deflection means, align the indentations 226 of the framework 220 with the renal arteries 102 so that the resulting scallops 240 are also properly aligned with the renal arteries 102. In particular, as the graft 210 is advanced along the length of the aorta 101 and the balloons 300 begin to deflect the flexible fabric 230, the balloons 300 engage the indentations 226 of the underlying framework 220. As the balloons 300 slide down the framework 220 and into the indentations 226, the balloons 300 cause the graft 210 to rotate so as to aligned the indentation 226 with the balloon 300 extending from the renal artery 102. As shown in FIG. 5A, the resulting scallops 240 formed within the indentation 226 are therefore aligned with the balloons 300 and no scallops are formed along the portion of the leading edge 232 where the balloons 300 are not present, as further discussed below.

Figure 4B:
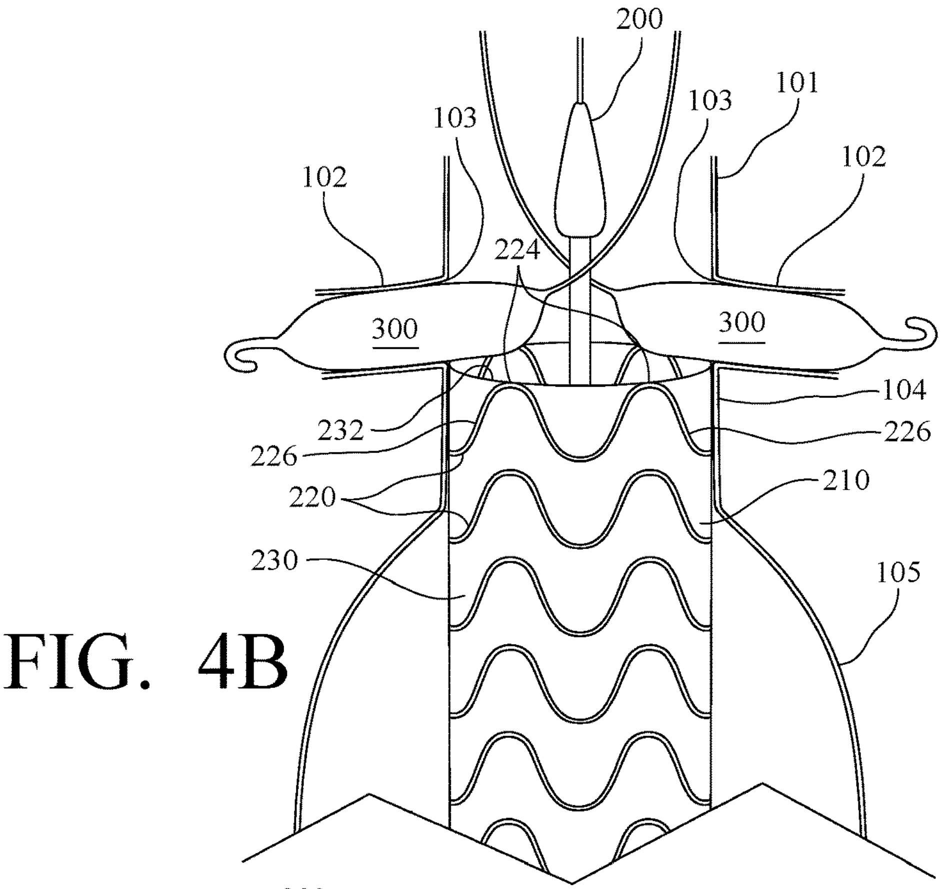
FIG. 4B depicts the proximal seal zone of FIG. 3 with two balloons, introduced by a proximal approach, positioned and inflated within each of the renal arteries.
Figure 5B:
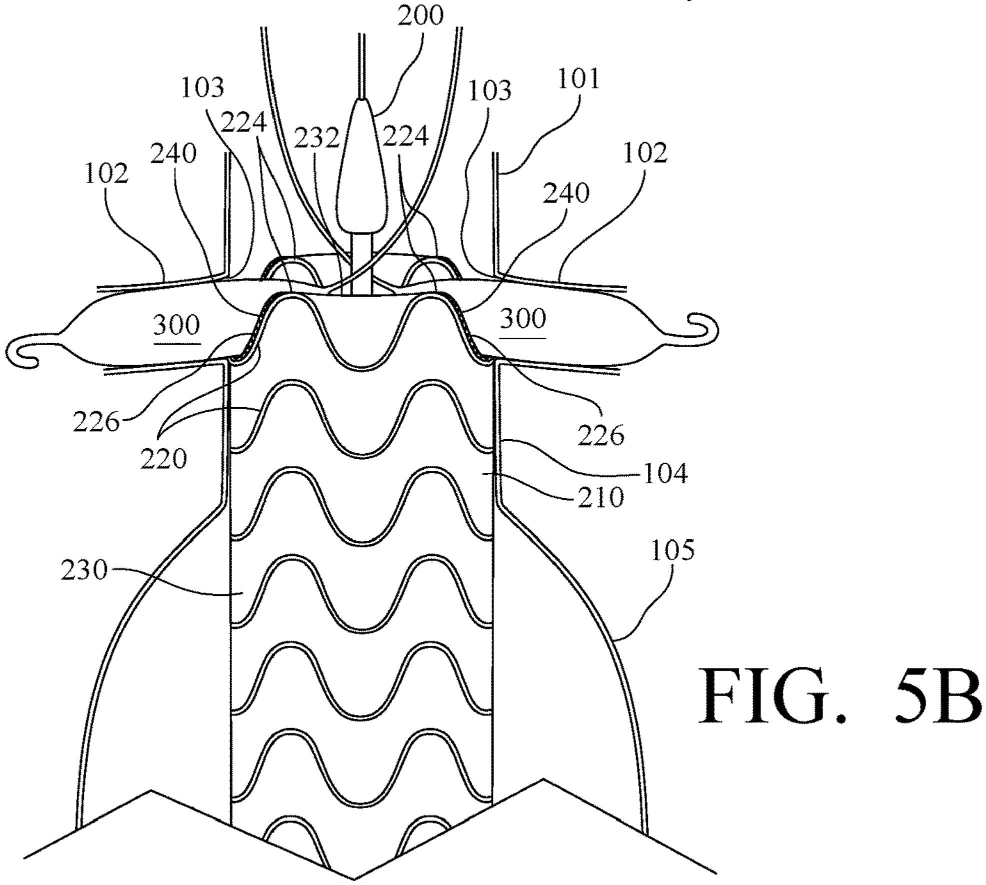
FIG. 5B depicts the proximal seal zone of FIG. 4B after the graft is advanced and each balloon has formed a scallop in the leading edge of the flexible fabric.

As shown in FIGS. 4A and 5A, in this exemplary implementation of the method of the present invention, the balloons 300 are introduced by a distal approach, such that the balloons 300 pass through the graft 210 itself before being positioned through the openings 103 of the renal arteries 102. Referring now specifically to FIGS. 4B and 5B, in another exemplary implementation of the present invention, the balloons 300 are introduced by a proximal approach. As shown in FIG. 5B, after the balloons 300 are positioned and inflated, the graft 210 is still advanced along the length of the aorta 101, such that the leading edge 232 of the flexible fabric 230 engages the balloons 300 forming the scallops 240 within the indentations 226 of the framework 220 while leaving the remainder of the leading edge 232 straight in substantially the same manner as discussed above with respect to FIGS. 4A and 5A.

Regardless of the particular direction of approach, it is contemplated that, rather than a balloon, the deflection means can be a sheath or other similar device known in the art which, after being introduced into the renal arteries 102, is capable of deflecting the leading edge 232 of the flexible fabric 230 when the graft 210 is advanced along the length of the aorta 101. Likewise, a cutting balloon or other similar device can be used to cut or tear the flexible fabric 230 in addition to, or instead of deflecting the leading edge 232 of the flexible fabric 230.

Referring once again to FIG. 3, in this exemplary implementation of the method of the present invention, the graft 210 is shown in a substantially deployed configuration within the aorta 101 such that the flexible fabric 230 of the graft 210 is adjacent to the inner wall of the aorta 101 with the leading edge 232 of the flexible fabric 230 immediately distal to the openings 103 of the renal arteries 102. Furthermore, in this exemplary implementation of the method of the present invention, the graft 210 remains in the substantially deployed configuration while the balloons 300 are positioned through the opening 103 of the renal arteries 102 (shown in FIGS. 4A and 4B) and while the graft 210 is advanced along the length of the aorta 101 (shown in FIGS. 5A and 5B). In some other exemplary implementations, however, a dual stage graft can be used, in which the graft is first partially deployed within the aorta, allowing for adjustments in the position of the graft. The graft is then fully deployed at which point the graft is effectively connected to the aorta with a sufficient seal between the graft and the inner wall of the aorta. For example, in some particular embodiments, a dual stage graft is partially deployed prior to positioning the balloons, or other similar deflection means, within the openings of the renal arteries. The dual stage graft is then fully deployed after the scallops are formed along the leading edge of the endoluminal graft. Of course, depending on the particular form of the graft provided, other variations in the order of the steps of positioning the graft, positioning the deflection means, advancing the graft, forming the scallops, and deploying the graft are also contemplated without departing from the spirit and scope of the present invention.

Figure 6:
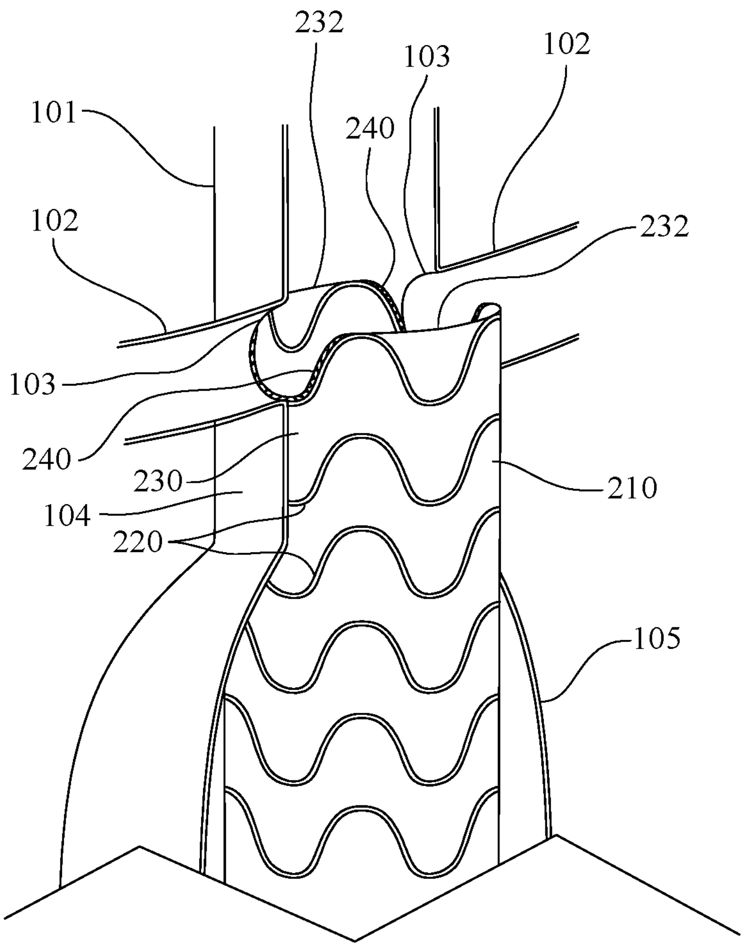
FIG. 6 is an oblique view of the graft of FIG. 5A after the balloons are removed showing the scallops aligned with the openings to the renal arteries.

Regardless of the particular implementation of the method of forming the scallops of the present invention, and referring now specifically to FIG. 6, after the scallops 240 are formed along the leading edge 232 of the graft 210, the balloons 300 are deflated and removed from the openings 103 to the renal arteries 102. The graft 210 is now positioned within the aorta 101 with a proximal seal made in the healthy portion 104 of the aorta 101 proximal to the aneurysm 105. Advantageously, in the exemplary system and method of the present invention, it is only the portion (or portions) of the leading edge 232 of graft 210 which is aligned with the openings 103 to the renal arteries 102 (i.e., where the balloons 300 were previously positioned) that is deflected to create the scallops 240. The remaining portion of the leading edge 232 is not deflected and extends above the openings 103 to the renal arteries 102. As such, even though the aneurysm 105 shown in FIGS. 3-6 is relatively close to the renal arteries 102, the area of the flexible fabric 230 in contact with the healthy portion 104 of the aorta 101 provides a sufficient seal while still preserving blood flow to the renal arteries 102.

Figure 7:
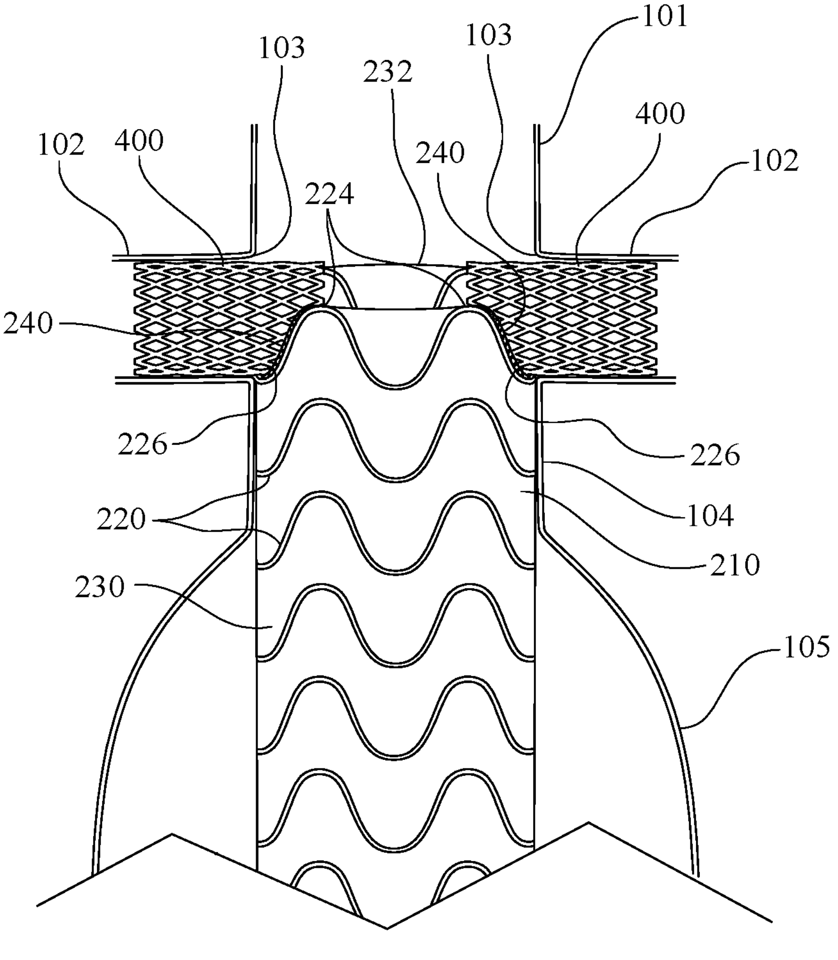
FIG. 7 depicts the proximal seal zone of FIG. 5A with stents deployed in each of the renal arteries.

In addition to the graft 210 described above, and referring now to FIG. 7, in some exemplary embodiments of the present invention, the system further includes stents 400 which are positioned adjacent to the scallop 240 of the graft 210 and extending through the opening 103 to the renal artery 102. In particular, in some exemplary implementations of the method of the present invention, the stents 400 are positioned after the scallops 240 are formed and the balloons 300 are deflated and removed from the openings 103. It is contemplated that the stents 400 help maintain the shape and alignment of the scallops 240, thus limiting the possibility of a subsequent decrease in flow to the renal arteries 102 caused, for example, by a shift in the position of the graft 210 within the aorta 101. The stents 400 included in the system of the present invention can be any one of a number of stents known in the art.

Referring now to FIGS. 8-11, in another exemplary embodiment of the system of the present invention, a delivery catheter 1200 and endoluminal graft 1210 are provided similar to the delivery catheter 200 and endoluminal graft 210 described above with respect to FIGS. 3-6, except the delivery catheter 1200 shown in FIGS. 8-11 further includes a plurality of tethers 1250 that connect the nosecone 1204 of the delivery catheter 1200 to the peaks 1224 of the metal framework 1220 of the graft 1210. With respect to the graft 1210 in particular, similar to the graft 210 described above, the graft 1210 shown in FIGS. 8-11 comprises a framework 1220 of curvilinear elements and a flexible fabric 1230 surrounding the framework 1220. The uppermost curvilinear element of the framework 1220 includes a plurality of alternating peaks 1224 and indentations 1226 with a leading edge 1232 of the flexible fabric 1230 extending between the peaks 1224 substantially flat across the indentations 1226 defined by the framework 1220 of the graft 1210.

The delivery catheter 1200 is also substantially the same as the delivery catheter 200 described above with respect to FIGS. 3-6 and includes a nose cone 1204 which is advanced along a guidewire 1202 and which precedes a guidewire lumen 1206 that is disposed around the guidewire 1202, but, as previously mentioned, the system shown in FIGS. 8-11 includes a plurality of tethers 1250 that connect the peaks 1224 of the metal framework 1220 of the graft 1210 to the nosecone 1204 of the delivery catheter 1200. The tethers 1250 provide a connection between the delivery catheter 1200 and the leading edge 1232 of the graft 1210 which facilitates the placement of the graft 1210 and formation of the scallops 1240, as discussed below.

Figure 8:
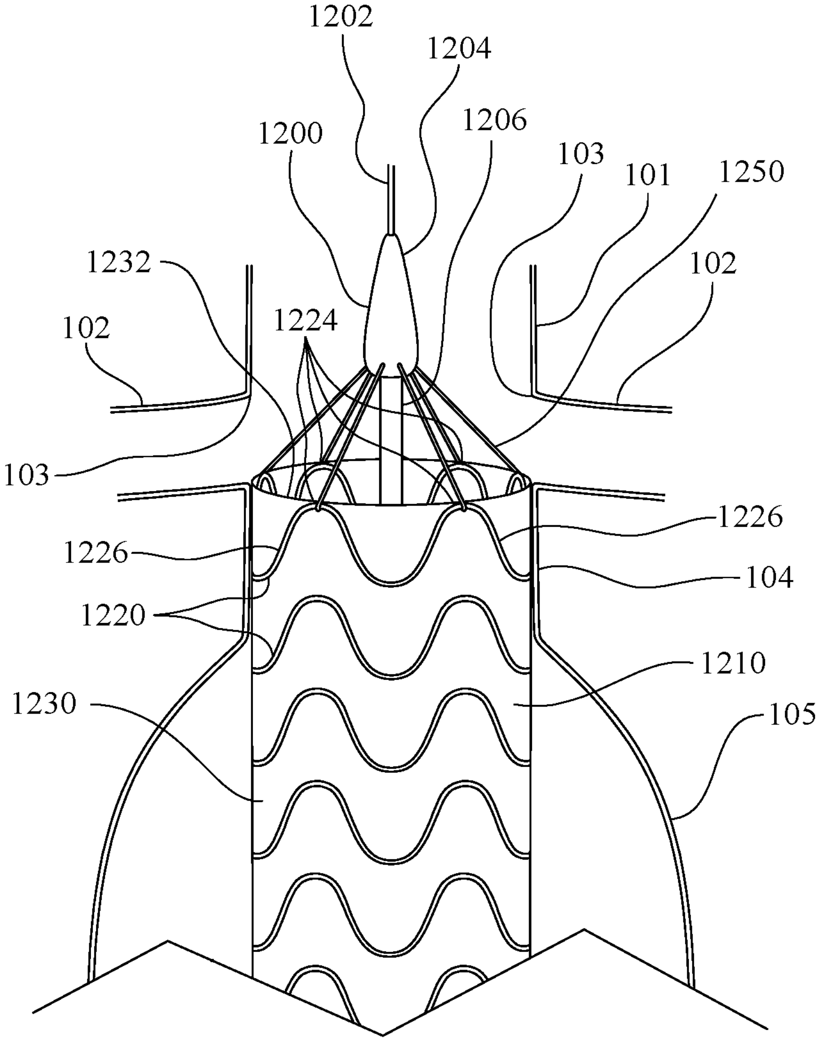
FIG. 8 depicts a proximal seal zone of another exemplary endoluminal graft of the present invention positioned via a delivery catheter having a plurality of tethers.

Referring now specifically to FIG. 8, the graft 1210 is initially positioned within the aorta 101 in substantially the same manner as described above with respect to FIG. 3 except that the tethers 1250 provide additional control in the placement of the leading edge 1232 adjacent to the openings 103 of the renal arteries 102. Specifically, by advancing the guidewire lumen 1206 along the guidewire 1202, the nose cone 1204 is also advanced, which, in turn pulls the graft 1210 along the length of the aorta 101 by way of the tethers 1250. As such, the graft 1210 can advantageously be advanced by a pulling mechanism in addition to a pushing mechanism.

Figure 9:
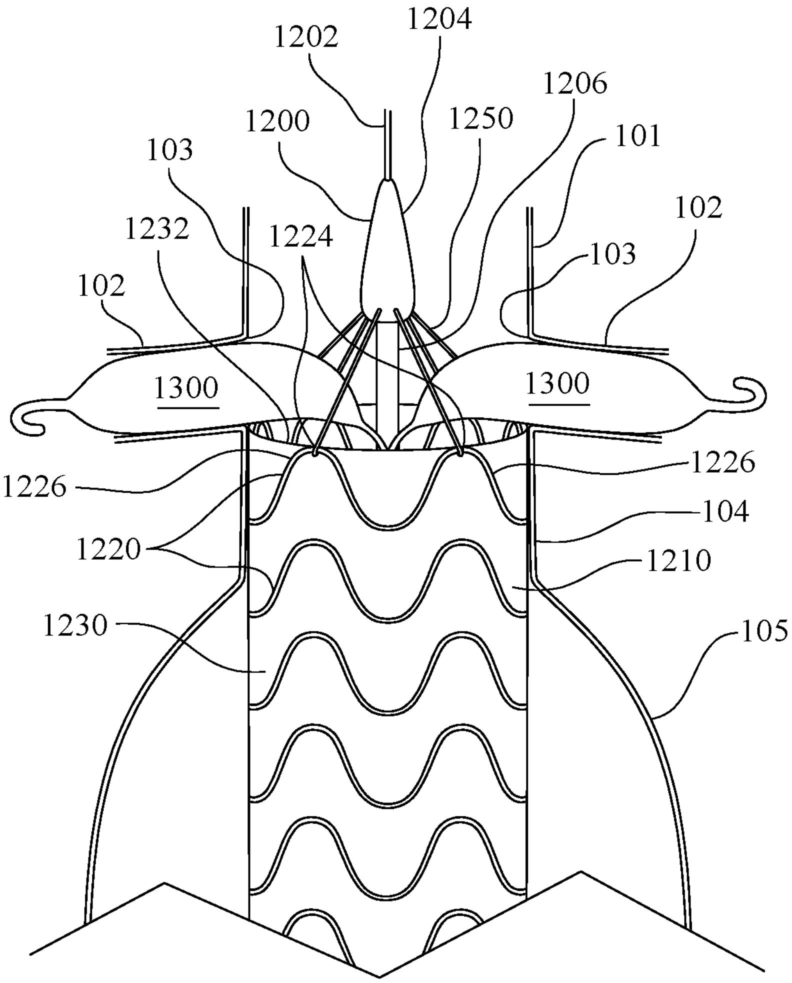
FIG. 9 depicts the proximal seal zone of FIG. 8 with two balloons, introduced by a distal approach, positioned and inflated within each of the renal arteries.

Referring now to FIG. 9, after positioning the graft 1210, a balloon 1300, is positioned through the opening 103 of each of the renal arteries 102 and subsequently inflated, in substantially the same manner as describe above with respect to FIG. 4A. Of note, in the exemplary implementation shown in FIG. 9, the balloons 1300 are introduced with a distal approach such that the balloons 1300 pass through the graft 1210 itself before being passed between two of the tethers 1250 and positioned through the openings 103 of the renal arteries 102. In other implementations of the present invention, however, the balloons 1300 are instead introduced by a proximal approach in substantially the same manner as described above with respect to FIG. 4B.

Figure 10:
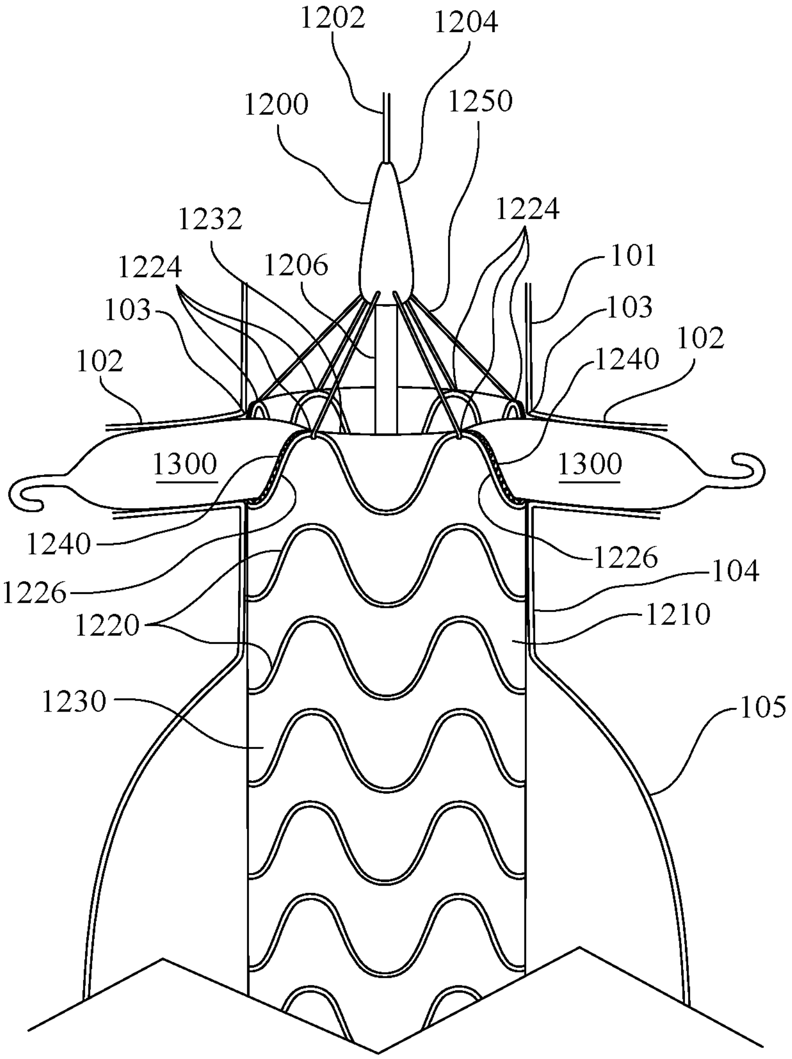
FIG. 10 depicts the proximal seal zone of FIG. 9 after the graft is advanced and each balloon has formed a scallop in the leading edge of the flexible fabric.

Regardless, and referring now to FIG. 10, after the balloons 1300 are positioned and inflated, the graft 1210 is advanced along the length of the aorta 101, such that the balloons 1300 engage the leading edge 1232 of the flexible fabric 1230 and cause the flexible fabric 1230 to deflect and form scallops 1240 along the leading edge 1232 and within the indentation 1226 of the framework 1220 in substantially the same manner as described above with respect to FIG. 5A. As mentioned above, the tethers 1250 provide additional control when forming the scallops 1240 by allowing the graft 1210 to be pulled upward by the plurality of tethers 1250, as opposed to simply being pushed upward. Except where stated otherwise above, all other aspects of the system and method of the present invention shown and described above with respect to FIGS. 8-10 are substantially the same as described above with respect to FIGS. 3-6.

Figure 11:
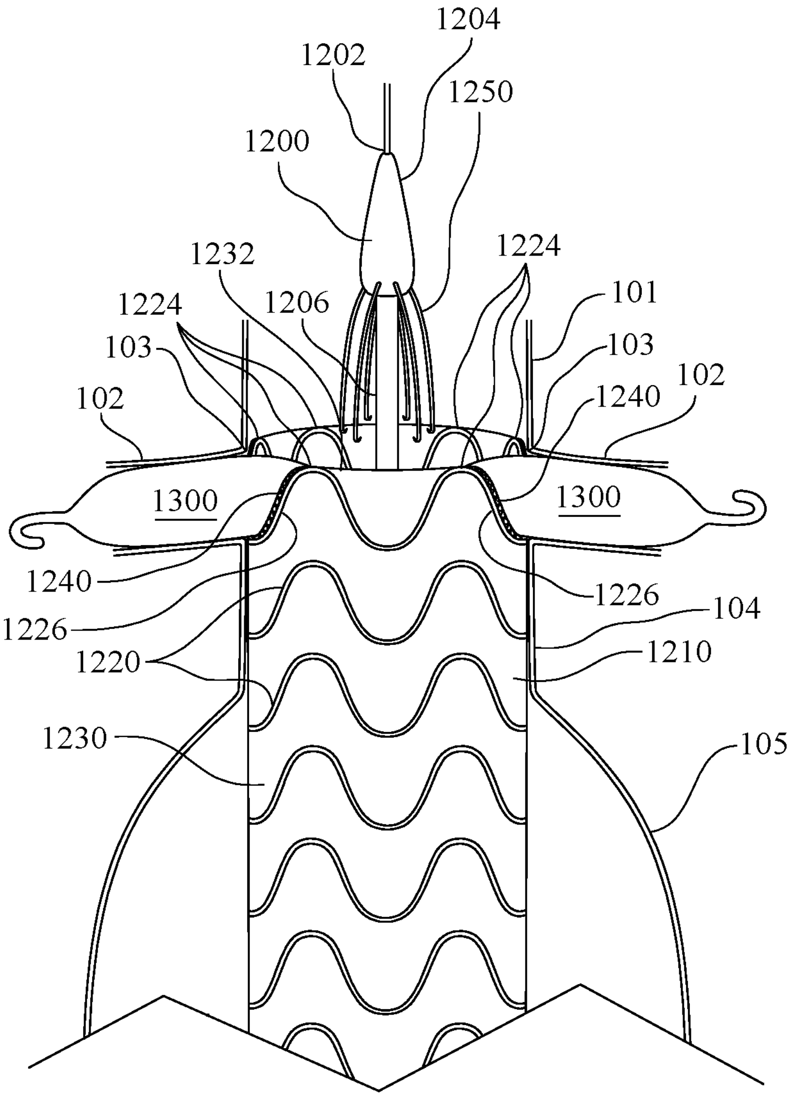
FIG. 11 depicts the proximal seal zone of FIG. 10 after the tethers are detached.

Referring now to FIG. 11, as a further refinement of the present invention, it is contemplated that, in some embodiments, the tethers 1250 are selectively connected to the peaks 1224 of the framework 1220 of the graft 1210. As such, the tethers 1250 can subsequently detach from the graft 1210 for removal along with the delivery catheter 1200 after forming the scallops 1240.

Figure 12:
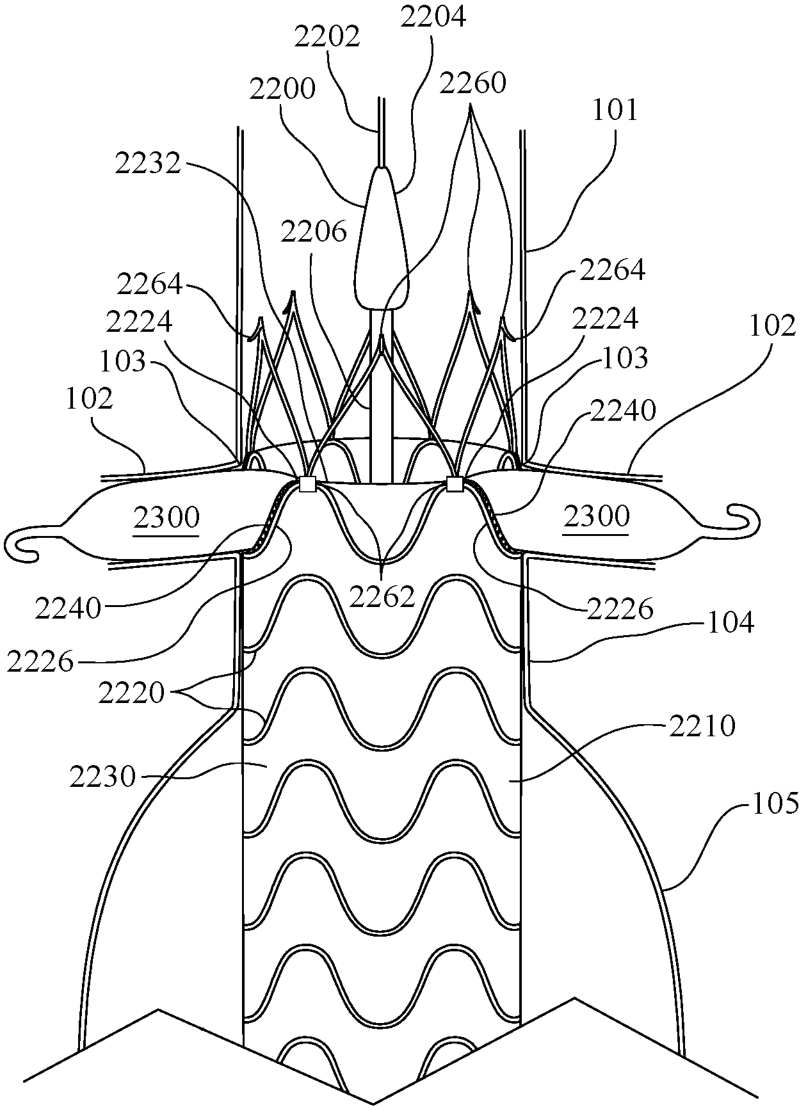
FIG. 12 depicts a proximal seal zone of another exemplary endoluminal graft of the present invention with two balloons, introduced by a distal approach, positioned and inflated within each of the renal arteries.

Referring now to FIG. 12, in another exemplary embodiment of the present invention, an exemplary endoluminal graft 2210 is provided similar to the exemplary endoluminal graft 210 described above with respect to FIGS. 3-6, except the graft 2210 shown in FIG. 12 further includes a plurality of transrenal fixation portions 2260 which are secured to the healthy portion 104 of the aorta 101 distal of the graft 2210, thus further assuring that the graft 2210 is effectively secured to the healthy portion 104 of the aorta 101 and an effective seal is formed proximal to the aneurysm 105. With respect to the graft 2210 in particular, and similar to the exemplary grafts 210, 1210 described above, the graft 2210 shown in FIG. 12 comprises a framework 2220 of curvilinear elements and a flexible fabric 2230 surrounding the framework 2220. The uppermost curvilinear element of the framework 2220 includes a plurality of alternating peaks 2224 and indentations 2226 with a leading edge 2232 of the flexible fabric 2230 that initially extends between the peaks 2224 substantially flat across the indentations 2226 defined by the framework 2220 of the graft 2210 and which ultimately forms the scallops 2240 in the indentations 2226 shown in FIG. 12. The delivery catheter 2200 shown in FIG. 12 is also substantially the same as the delivery catheter 200 described above with respect to FIGS. 3-6 and includes a nose cone 2204 which is advanced along a guidewire 2202 and which precedes a guidewire lumen 2206 that is disposed around the guidewire 2202. In the embodiment shown in FIG. 12, each of the transrenal fixation portions 2260 are connected to two adjacent peaks 2224 of the framework 2220 of the graft 2210 and extend away from the leading edge 2232, terminating at a hook 2264 configured to engage the interior wall of the healthy portion 140 of the aorta 101 when deployed.

Referring still to FIG. 12, with the inclusion of the transrenal fixation portions 2260, each of the balloons 2300 must pass through one of the transrenal fixation portions 2260 and above the leading edge 2232 of the flexible fabric 2230 when being positioned through the openings 103 of each of the renal arteries 102. In at least some embodiments, the flexible fabric 2230 of the graft 2210 is radiographically "invisible" making it difficult to determine the exact position of the leading edge 2232 of the flexible fabric 2230 and, therefore, the position of the balloons 2300 in relation to the leading edge 2232 of the flexible fabric 2230. As such, in this exemplary embodiment shown in FIG. 12, a plurality of radiographic markers 2262 are positioned at the intersection of the transrenal fixation portions 2260 and the peaks 2224 of the metal framework 2220. The radiographic markers 2262 allow an operate to visually monitor the position of the markers 2262, and thus the leading edge 2232 of the flexible fabric 2230, in relation to the balloons 2300 and/or renal arteries 102 to ensure that the balloons 2300 extend between one of the transrenal fixation portions 2260 and the leading edge 2232 of the flexible fabric 2230. As shown in FIG. 12, when the scallops 2240 are formed, the balloons 2300 are substantially below the line of markers 2262 and therefore, an operator can ensure that the scallops 2240 are appropriately formed within the indentations 2226 of the metal framework 2220 of the graft 2210. Except where stated otherwise above, all other aspects of the system and method of the present invention shown and described above with respect to FIG. 12 are substantially the same as the system and method described above with respect to FIGS. 3-6.

Figure 13:
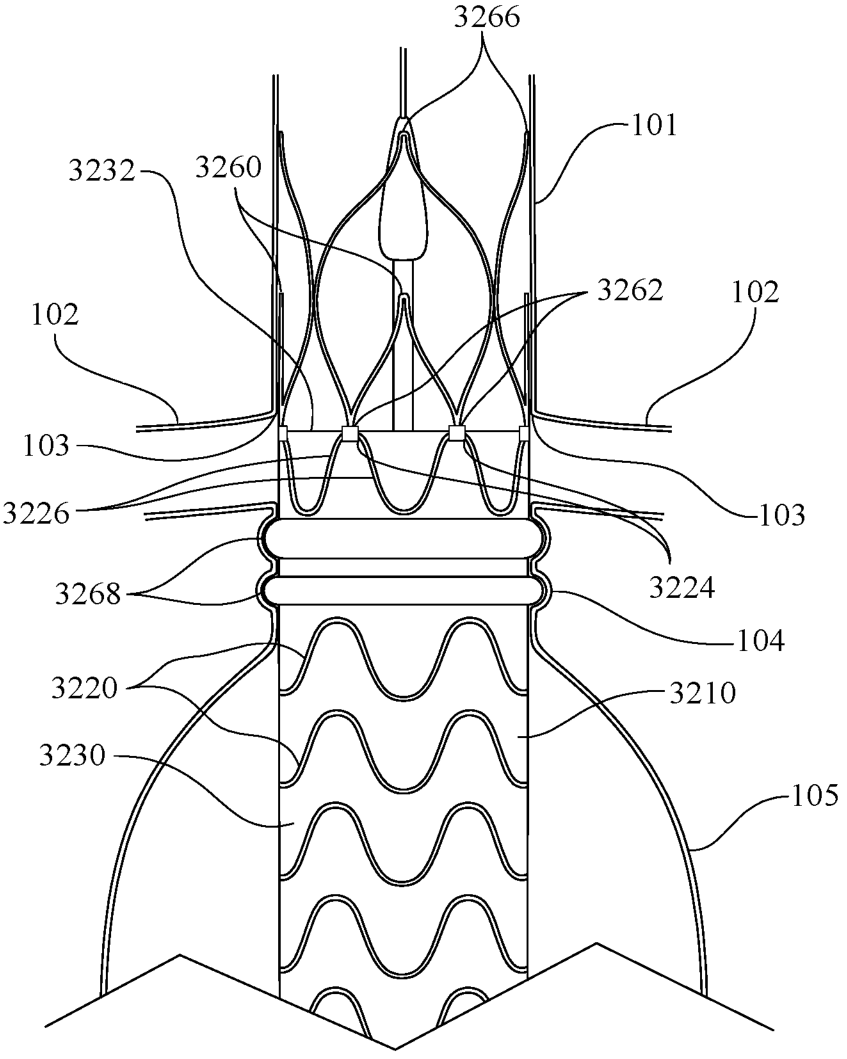
FIG. 13 depicts a proximal seal zone of another exemplary endoluminal graft of the present invention.

Referring now to FIG. 13, in another exemplary system of the present invention, an endoluminal graft 3210 is provided which includes additional features which assist in securing the graft 3210 to the healthy portion 104 of the aorta 101 and a forming an effective seal proximal to the aneurysm 105. Similar to the exemplary endoluminal grafts 210, 1210, 2210 described above, the endoluminal graft 3210 shown in FIG. 13 comprises a framework 3220 of curvilinear elements and a flexible fabric 3230 surrounding the framework 3220. The uppermost curvilinear element of the framework 3220 includes a plurality of alternating peaks 3224 and indentations 3226 with a leading edge 3232 of the flexible fabric 3230 initially extending between the peaks 3224 substantially flat across the indentations 3226 defined by the framework 3220 of the graft 3210. Furthermore, and similar to the exemplary graft 2210 shown in FIG. 12, the graft 3210 shown in FIG. 13, further includes transrenal fixation portions 3260, 3266 as well as a plurality of radiographic markers 3262. The radiographic markers 3262 shown in FIG. 13 are substantially similar to the radiographic markers 2262 described above with respect to FIG. 12, but the transrenal fixation portions 3260, 3266 comprise both a mid-crown of fixation portions 3260 and a top-crown of fixation portions 3266. Furthermore, unlike any of the previously describe grafts, the graft 3210 shown in FIG. 13 also includes two sealing rings 3268 which are injectable with a polymer. One such exemplary graft 3210 is the OVATION® graft which is produced by TriVascular, Inc. of Santa Rosa, California (OVATION® is a registered trademark of TriVascular, Inc. of Santa Rosa, California).

In an exemplary implementation of the method of the present invention which uses a graft 3210 having both a mid-crown 3260 and a top-crown 3266 of fixation portions, the first step of deploying the graft 3210 is to release the mid-crown of fixation portions 3260. A balloon (not shown) is passed through one of the fixation portions 3260 of the mid-crown and above the leading edge 3232 of the flexible fabric 3230 when being positioned through the opening 103 of the renal artery 102. The balloon is then inflated and the scallop (not visible) is formed substantially as described above. The top-crown of fixation portions 3266 is then released, securing the graft 3210 in place in the aorta 101. Finally, polymer is injected into the sealing rings 3268 as well as other channels built into the graft 3210 forming a seal with the healthy portion 104 of the aorta 101. Except where stated otherwise above, all other aspects of the system and method of the present invention shown and described above with respect to FIG. 13 are substantially the same as the system and method described above with respect to FIGS. 3-6.

Figure 14:
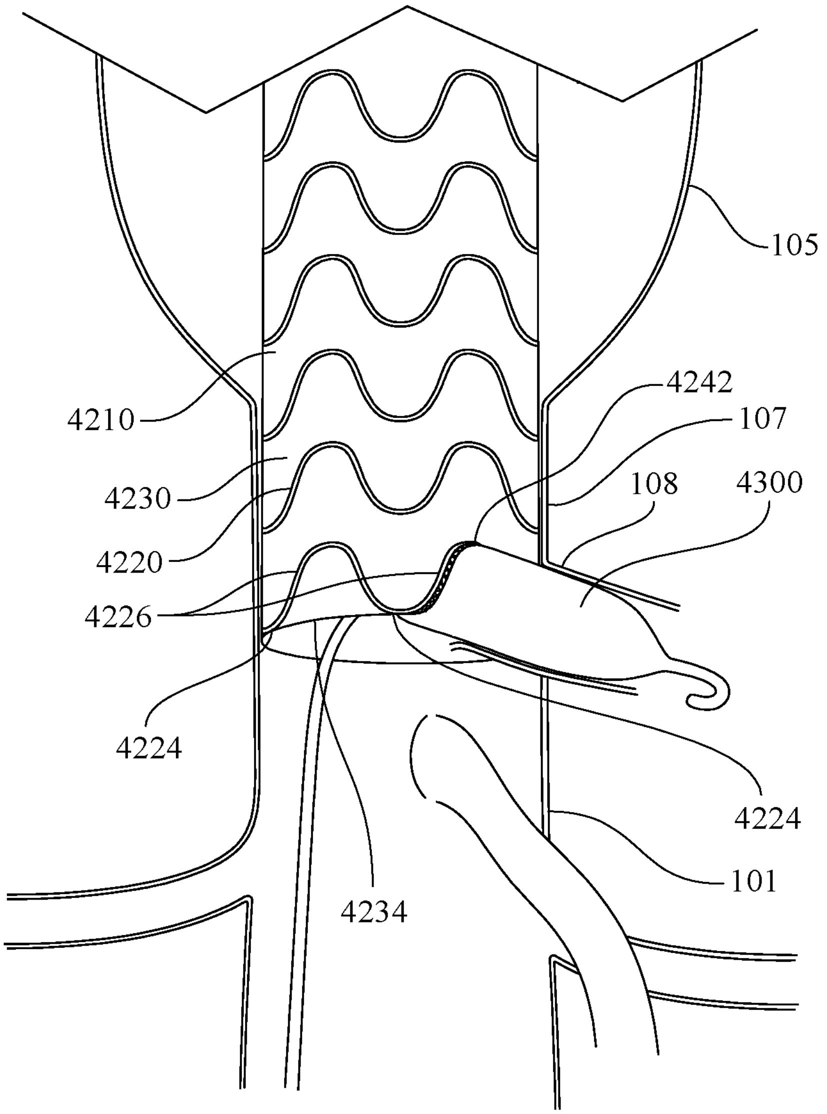
FIG. 14 depicts a distal seal zone of another exemplary endoluminal graft of the present invention with a scallop aligned with the opening to a branching artery.

Referring now to FIG. 14, in another exemplary implementation of the method of the present invention, a scallop 4242 is formed at the distal seal zone of another exemplary endoluminal graft 4210. The endoluminal graft 4210 is substantially the same as the endoluminal graft 210 described above with respect to FIGS. 3-6 except that the scallop 4242 is formed at a distal edge 4234 of the graft 4210. With respect to the graft 4210 in particular, similar to the graft 210 described above, the graft 4210 shown in FIG. 14 comprises a framework 4220 of curvilinear elements and a flexible fabric 4230 surrounding the framework 4220. The lowermost curvilinear element of the framework 4220 includes a plurality of alternating peaks 4224 and indentations 4226 with a distal edge 4234 of the flexible fabric 4230 initially extending between the peaks 4224 substantially flat across the indentations 4226 defined by the framework 4220 of the graft 4210. In an exemplary implementation of the method of the present invention, the graft 4210 is first positioned within the aorta 101 and extending through the aneurysm 105 and into a healthy portion 107 of the aorta 101 distal to the aneurysm 105 with the distal edge 4234 of the flexible fabric 4230 positioned adjacent to an opening to a branching artery 108. Next, a balloon 4300 is positioned through the opening to the branching artery 108 and subsequently inflated and the graft 4210 is advanced along the length of the aorta 101, such that the balloon 4300 engages the distal edge 4234 of the flexible fabric 4230 causing the flexible fabric 4230 to deflect and form a scallop 4242 in substantially the same manner previously discussed. After securing the graft 4210 in place, the balloon 4300 is then deflated and removed.

Although the above implementations of the exemplary method of the present invention are described with respect to implanting the endoluminal graft within the aorta of a patient, it is of course, understood that similar methods are applicable to other blood vessels of the patient where an aneurism, or other similarly diseased portion of the blood vessel, is positioned near one or more branching arteries.

One of ordinary skill in the art will recognize that additional embodiments are possible without departing from the teachings of the present invention. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the present invention.

What is claimed is:

1. An endoluminal graft system, comprising:

an endoluminal graft configured for placement within a primary vessel and including a framework and a flexible fabric surrounding the framework, the flexible fabric defining a leading edge;

a deflection means configured for placement through an opening to a branching vessel;

a delivery catheter configured to position the endoluminal graft within the primary vessel with the leading edge of the flexible fabric adjacent to the opening to the branching vessel, the delivery catheter further configured to advance the endoluminal graft along the length of the primary vessel after the deflection means is positioned through the opening to the branching vessel such that the deflection means engages the leading edge of the flexible fabric and forms a scallop in situ along the leading edge of the flexible fabric;

wherein the endoluminal graft has an initial configuration in which the leading edge extends along a full circumference of the flexible fabric when the endoluminal graft is placed within the primary vessel.

2. The endoluminal graft system of claim 1, wherein the framework of the endoluminal graft defines a plurality of indentations adjacent to the leading edge of the flexible fabric and the scallop is formed within one of the plurality of indentations.

3. The endoluminal graft system of claim 1, wherein the deflection means is a balloon configured to selectively inflate and deflate.

4. The endoluminal graft system of claim 1, and further comprising a stent configured to extend through the opening to the branching vessel adjacent to the scallop.

5. The endoluminal graft system of claim 1, wherein the delivery catheter includes a plurality of tethers selectively connected to the framework of the endoluminal graft, the plurality of tethers configured to advance the endoluminal graft along the length of the primary vessel and subsequently detach.

6. The endoluminal graft system of claim 1, wherein the endoluminal graft further includes one or more transrenal fixation portions connected to the framework and extending away from the leading edge of the flexible fabric.

* * * * *